(12) United States Patent
Tsaur

(10) Patent No.: US 7,674,759 B2
(45) Date of Patent: *Mar. 9, 2010

(54) STABLE LIQUID CLEANSING COMPOSITIONS CONTAINING HIGH LEVEL OF FATTY ACID ISETHIONATE SURFACTANT PRODUCTS HAVING MORE THAN 10 WT. % OF FATTY ACID/FATTY SOAP CONTENT

(75) Inventor: Liang Sheng Tsaur, Norwood, NJ (US)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/850,159

(22) Filed: Sep. 5, 2007

(65) Prior Publication Data

US 2009/0062177 A1    Mar. 5, 2009

(51) Int. Cl.
*C11D 17/00* (2006.01)
(52) U.S. Cl. .................. 510/424; 510/426; 510/427; 510/428; 510/499; 510/501
(58) Field of Classification Search ............... None
See application file for complete search history.

(56) References Cited

U.S. PATENT DOCUMENTS 3,723,325 A    3/1973    Parran, Jr.
4,565,647 A    1/1986    Llenado
5,009,814 A    4/1991    Kelkenberg et al.
5,132,037 A    7/1992    Greene et al.
5,234,619 A    8/1993    Greene et al.
5,290,471 A    3/1994    Greene et al.
5,389,279 A    2/1995    Au et al.
5,415,810 A    5/1995    Lee et al.
5,739,365 A    4/1998    Briody et al.
5,952,286 A    9/1999    Puvvada et al.
6,077,816 A    6/2000    Puvvada et al.
2004/0224863 A1    11/2004    Sun et al.

FOREIGN PATENT DOCUMENTS

EP    1 479 365    11/2004
WO    97/05857    2/1997
WO    99/32069    7/1999

OTHER PUBLICATIONS

Co-pending U.S. Appl. No. 11/613,617 to Tsaur et al. filed Dec. 20, 2006.

(Continued)

*Primary Examiner*—Necholus Ogden, Jr.
(74) *Attorney, Agent, or Firm*—Ronald A. Koatz

(57) ABSTRACT

The invention provides liquid cleanser compositions which contains fatty acyl isethionate surfactant products having at least 10 wt % free fatty acid and/or fatty acid salt used as the primary surfactant at a level at least 60 wt % of total fatty acyl isethionate and synthetic cosurfactants in the liquid composition. The key is to insure a specific combination of surfactant crystal modifiers so that the fatty acyl isethionate-containing liquid composition will be stable at low and high temperatures.

7 Claims, 3 Drawing Sheets

OTHER PUBLICATIONS

Co-pending U.S. Appl. No. 11/613,696 to Tsaur et al. filed Dec. 20, 2006.
Co-pending U.S. Appl. No. 11/613,666 to Tsaur et al. filed Dec. 20, 2006.
Co-pending U.S. Appl. No. 11/658,471 to Tsaur et al. filed Dec. 18, 2007.
XP-002474464, Oct. 1988, English abstract of JP 1987-0077976.
Co-pending application: Tsaur; U.S. Appl. No. 11/613,617, filed Dec. 20, 2006.
Co-pending application: Tsaur; U.S. Appl. No. 11/613,696, filed Dec. 20, 2006.
Co-pending application: Tsaur; U.S. Appl. No. 11/613,666, filed Dec. 20, 2006.
Co-pending application: Tsaur; U.S. Appl. No. 11/658,471, filed Dec. 17, 2007.
Co-pending application for: Applicant: Tsaur et al.; U.S. Appl. No. 12/235,955; filed Sep. 23, 2008, entitled Stable Cleansing Compositions Containing Fatty Acyl Isethionate Surfactant Products Having More Than 10 wt. % of Fatty Acid/Fatty Soap Content Using High Level of Polyol and Methods Thereof.

STABLE LIQUID CLEANSING COMPOSITIONS CONTAINING HIGH LEVEL OF FATTY ACID ISETHIONATE SURFACTANT PRODUCTS HAVING MORE THAN 10 WT. % OF FATTY ACID/FATTY SOAP CONTENT

FIELD OF THE INVENTION

The invention is directed to personal care skin or hair liquid cleansing compositions. In particular, it relates to such personal care skin or hair cleansing compositions comprising fatty acyl isethionate surfactants, as the primary surfactant, at a level of at least 60 wt % of total fatty isethionate surfactant product and other synthetic co-surfactants in the personal skin or hair liquid cleansing compositions. Commercially available fatty acyl isethionate surfactant products comprise a mixture of fatty acyl isethionates and free fatty acid/fatty soaps. The subject invention is directed to fatty acyl isethionate surfactant products having a defined range (starting at about 10%) of fatty acid/fatty soaps in the surfactant product, so that the total fatty acid in the isethionate surfactant product will always comprise at least 10%, preferably at least 15% of the fatty acyl isethionate surfactant product.

BACKGROUND OF THE INVENTION

Fatty acyl isethionates (e.g., cocoyl isethionates) are anionic surfactants highly desirable in personal care skin or hair cleansing products, particularly in personal care products, because they lather well, are mild to the skin and have good emollient properties. Typically, fatty acid isethionates are produced by esterification of fatty acids or by reaction of fatty acid chloride having carbon chain length of $C_8$ to $C_{20}$ with isethionate. A typical surfactant product (e.g., commercially sold or made surfactant product) containing fatty acyl isethionate contains about 40 to 95 wt. % fatty acyl isethionate, and 0 to 50 wt. %, typically 5 to 40 wt. % free fatty acid, in addition to isethionate salts, typically at less than 5%, and trace (less than 2 wt. %) of other impurities.

A problem with the ready use of commercially sold or made fatty acyl isethionate product in liquid compositions, wherein the acyl isethionate surfactant product is used as a primary surfactant comprising a level of at least 60% wt % of total fatty isethionate surfactant product and other synthetic surfactants in the liquid composition, however, is the low solubility of these compounds in water. This is especially true for fatty acyl isethionate surfactant product containing high level of free fatty acid/fatty soaps (10% by wt. or higher) and/or long chain fatty acyl isethionates component (e.g., $C_{14}$ and higher). The fatty acyl isethionate component of the surfactant product tends to form insoluble surfactant crystals with the amount of crystals depending strongly on the storage temperature due to the wide range of dissolution temperatures of these crystals. This in turn results in unstable liquid cleansers which exhibit very thick or very thin consistency at low and elevated temperatures. At low temperature, the liquid composition becomes a semi-solid gel which is difficult to use. At elevated temperature, the liquid composition turns into water-thin liquid which causes phase separation of the product.

It would therefore be of tremendous advantage to have compositions having consistent viscosity at both low and elevated temperatures; as well as a way of manipulating compositional ingredients to ensure such consistent viscosity is obtained and that fatty acyl isethionate product, no matter what their free fatty acid/fatty soap content or what the chain lengths of the fatty acyl isethionate, fatty acid or fatty acid soap component, can be readily used as the primary surfactant (comprising at least 60% of total surfactants) in a liquid cleanser composition. The present invention provides precisely such compositions and processes for making such compositions.

Specifically, the invention recognizes that the problem of inconsistent viscosity and physical instability can be resolved by converting part of the fatty acyl isethionate and fatty acid crystals to viscous surfactant liquid crystals at a temperature at or above the dissolution temperature of these long chain fatty acid and/or fatty acyl isethionate crystals such that the liquid composition in which the surfactant product will be used has a high enough viscosity to ensure stability, said stability being defined by the absence of visible physical separation after two weeks of storage at 45° C. This is accomplished by using an elevated temperature storage stabilizing system in the composition comprising a combination of (1) alkanolamide and/or alkylamineoxide and (2) an ingredient selected from the group consisting of ammonium salt, hydrocarbon oils, organic amine, fatty alcohol, fatty acid and mixture of the above ingredients. The compounds of the stability system are believed to modify the surfactant crystal and creates a more consistent viscosity which allows fatty acyl isethionate product, regardless of free fatty acid content or the chain length of isethionates, fatty acids, and/or fatty acid soaps to have more consistent viscosity at both low and elevated temperatures and to thereby be storage stable.

Acyl isethionate liquids do exist in the art. U.S. Pat. No. 5,415,810 to Lee et al., for example, discloses compositions comprising fatty acyl isethionates and zwitterionic surfactant (e.g., cocoamidopropyl betaines), presumably to help solubilize the isethionate and make an isotropic liquid. The reference separately teaches away from use of both alkanolamides (column 1, lines 27-30), and use of free fatty acids, especially longer chain fatty acids (column 2, lines 34-39), let alone the use of both specifically in combination.

U.S. Pat. No. 5,739,365 to Brody et al. and U.S. Publication No. 2004/0224863 both disclose use of synthetic surfactants having ammonium counterion to help solubilize fatty acid isethionate.

U.S. Pat. No. 5,132,037 to Greene et al. (and related U.S. Pat. No. 5,234,619 and U.S. Pat. No. 5,290,471) disclose compositions with $C_8$ to $C_{22}$ acyl isethionates, synthetics, and free fatty acid, preferably $C_{16}$ or higher. The alkanolamide and/or alkylamineoxide surfactant crystal modifiers of the subject invention are not disclosed; nor is a process to use both these modifiers and second ingredient specifically together to provide long term stabilization system for the acyl isethionates.

U.S. Pat. No. 5,952,286 and U.S. Pat. No. 6,077,816, both to Puvvada, disclose liquid cleansing compositions which may contain acyl isethionates and which comprise soluble, lamellar phase inducing structurant (e.g., branched fatty acid). While amides may be optionally used in a long recitation of optional ingredients, there is no teaching or disclosure that they need be used; that they must be used in combination with a alkanolamide and/or alkylamineoxide to provide acyl isethionate stabilization system; let alone that the ingredients of the stabilization system must be used in certain minimal amounts.

Applicants filed in December 2006 three cases relating to liquid compositions with crystal modifier systems similar to those of the subject invention. It would not have been predictable in any of these applications, however, that the modifier could be used or would function in compositions where the fatty acyl isethionate surfactant product comprises 60% or more of the surfactant system by forming viscous surfactant liquid crystals upon the dissolution of fatty acyl isethionate/fatty acid crystals at elevated temperatures (40° C. or above).

None of the references, alone or together, teach or suggest compositions comprising fatty acyl isethionate surfactant product as the primary surfactant at a level of at least 60 wt %, preferably 70 wt % of total fatty acyl isethionate surfactant product and other synthetic surfactants in the liquid composition where acyl isethionate/fatty acid crystals formed at room temperature are partially converted to viscous surfactant liquid crystals at elevated temperatures (40 C or above) upon the dissolution of the acyl isethionate/fatty acid crystals using specific surfactant crystal modifier system/stabilization system comprising a combination of alkanolamide and/or alkylamine oxide together with an ingredient selected from the group consisting of ammonium salt, organic amine, hydrocarbon oils, fatty alcohols, fatty acids and mixtures thereof in order to provide acyl isethionate containing liquids, regardless of the fatty acid content or fatty acid chain length of the acyl isethionates surfactant, free fatty acid or fatty acid soap; the compositions formed have a product viscosity less sensitive to temperature, and are stable at elevated temperature storage conditions.

BRIEF SUMMARY OF THE INVENTION

In one embodiment, the present invention relates to novel liquid cleansing compositions containing fatty acyl isethionate surfactant product at a level of at least 60%, preferably at least 70 wt % of total fatty acyl isethionate surfactant product and cosurfactant in the composition which are stabilized with a specific combination of surfactant structure modifiers used to increase the viscosity of the liquid composition at elevated temperatures.

More specifically, the invention comprises liquid cleansing compositions comprising:
  (a) 15 to 50 wt % of fatty acyl isethionate surfactant product containing 10 to 50 wt % fatty acids and/or fatty soaps and 35 to 85 wt % fatty acyl isethionate in the said product, said product comprising at least 60% of total surfactant product of item a and co-surfactants of item b in the liquid composition;
  (b) 0 to 15 wt % of a co-surfactant selected from the group consisting of anionic (excluding fatty acyl isethionate of (a)), amphoteric and nonionic surfactants and mixture thereof wherein the amount of said cosurfactant is 0 to 40 wt % of total amount of fatty acyl isethionate surfactant product of item a and cosurfactant of item b; and
  (c) 1% and above of an elevated temperature stabilizing system comprising:
    (i) 0.1 to 8 wt % of a compound selected from the group consisting alkanolamide, alkylamineoxide and mixture of above;
    (ii) 0.3 to 8 wt % of a compound selected from the group consisting of C9 to C30 aliphatic hydrocarbon oils, ammonium salt, organic amine, linear C8 to C13 fatty acid/fatty alcohol, branched fatty acid and mixtures thereof, wherein the total amount of fatty alcohols and branched fatty acids is no more than 2 wt % in the liquid composition (due to potential effect on lather);
  wherein the ratio of fatty acyl isethionate surfactant product of item a to cosurfactant of item b is in the range of 10/0 to 6/4; the viscosity of the said liquid cleanser composition at $0.01\ s^{-1}$ should be at least 250 Pas, preferably at least 350 Pas at 25° C.; and the ratio of the viscosity at 40° C. to the viscosity at 25° C., when measured at $0.01\ s^{-1}$, should be at least 0.1, preferably 0.2, most preferably 0.4; wherein said composition is stable (i.e., is physically stable and will not partition as can be visually observed) at 45° C. for at least 2 weeks.

At ambient temperature, the said composition contains surfactant crystals with dissolution temperature between 30° C. to 50° C.

In a second embodiment, the invention relates to a process for making such compositions using fatty acyl isethionate surfactant product, co-surfactant, and the elevated temperature storage stability system as noted above.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
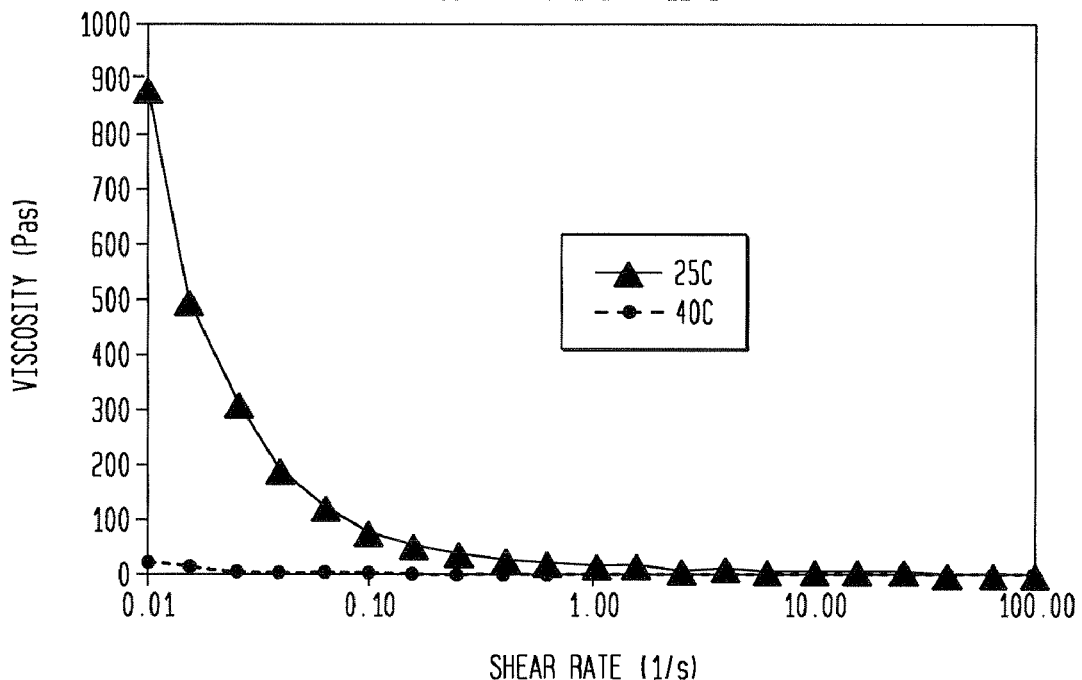
FIG. 1 is temperature effect on the viscosity profile of liquid composition containing only fatty acyl isethionate surfactant product without the specific elevated temperature stabilizing system of this invention (comparative example 1A of Table 2). The figure shows that the sample has a viscosity very sensitive to the storage temperature. At 25° C., it has 875 Pas viscosity at $0.01\ S^{-1}$ with lotion-like consistency. At 40° C., it became a water-thin liquid with a viscosity of only 23 Pas at $0.01\ S^{-1}$. The viscosity ratio of 40° C. to 25° C. is 0.026 and the sample showed phase separation at 45° C. storage condition in less than 1 week.
Figure 2:
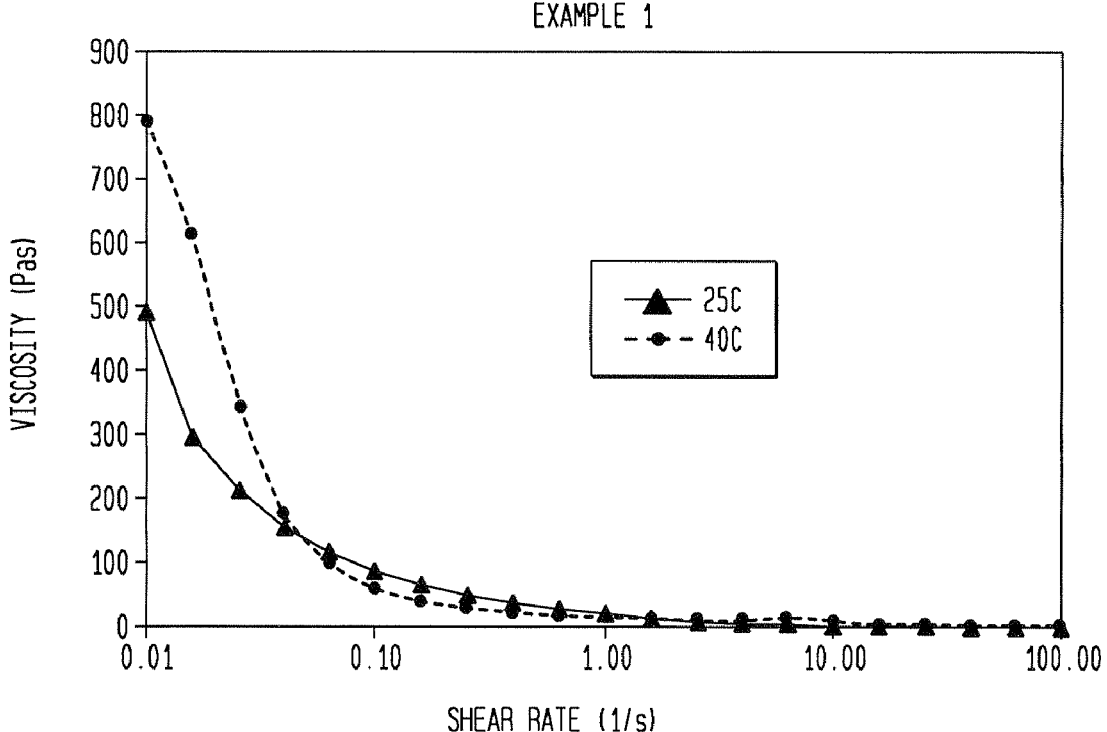
FIG. 2 is a viscosity profile of liquid composition containing fatty acyl isethionate surfactant product at the level same as the one shown in FIG. 1 with the surfactant crystal modifiers forming stabilizing system of this invention, i.e. combination of cocomonoethanolamide and ammonium sulfate, which is Example 1 of Table 1. The sample at 40° C. had a viscosity higher than the one at 25° C. with a viscosity ratio of 40° C. to 25° C. equal to 1.61 (measured at $0.01\ S^{-1}$). The sample was stable at both ambient and 45° C. for over 4 weeks.

The present invention relates to novel liquid cleansing compositions comprising fatty acyl isethionate as the primary surfactant at a level at least 60 wt %, preferably at least 70 wt % of total fatty acyl isethionate surfactant product and cosurfactants in the composition. The compositions are viscous and very stable regardless of the level of free fatty acid of starting surfactant (e.g., 10-50% in this invention) or the chain lengths of the fatty acyl isethionates, free fatty acids and/or fatty acid (factors which typically affect stability and viscosity of compositions comprising acyl isethionates, especially at low and elevated temperature).

More specifically, the invention comprises liquid cleansing compositions comprising:

(a) 15 to 50 wt % of fatty acyl isethionate surfactant product containing 10 to 50 wt % fatty acids and/or fatty soaps and 35 to 85 wt % fatty acyl isethionate in the said product, said product comprising at least 60% of total surfactant product of item a and co-surfactants of item b in the liquid composition;

(b) 0 to 15% wt % of a co-surfactant selected from the group consisting of anionic (excluding fatty acyl isethionate of (a)), amphoteric and nonionic surfactants and mixture thereof wherein the amount of said cosurfactant is 0 to 40 wt % of total amount of fatty acyl isethionate surfactant product of item a and cosurfactant of item b;

(c) 1% and above of an elevated temperature stabilizing system comprising:

(i) 0.1 to 8 wt % of a compound selected from the group consisting of alkanolamide, alkylamineoxide and mixture of above;

(ii) 0.1 to 8 wt % of a compound selected from the group consisting of C9 to C30 aliphatic hydrocarbon oils, ammonium salt, organic amine, linear C8 to C13 fatty acid/fatty alcohol, branched fatty acid and mixtures thereof wherein the total amount of fatty alcohols and branched fatty acids is no more than 2 wt % in the liquid composition;

wherein the ratio of fatty acyl isethionate surfactant product of item a to cosurfactant of item b is in the range of 10/0 to 6/4; the viscosity of the said liquid cleanser composition at 0.01 s$^{-1}$ should be at least 250 Pas, preferably at least 350 Pas at 25° C.; and the ratio of the viscosity at 40° C. to the viscosity at 25° C., when measured at 0.01 s$^{-1}$, should be at least 0.1, preferably 0.2, most preferably 0.4 and above (the higher the ratio, the better for stability), wherein said composition is stable (i.e., is physically stable and will not partition as can be visually observed) at 45° C. for at least 2 weeks.

At ambient temperature, the said composition contains surfactant crystals with dissolution temperature between 30° C. to 50° C.

The invention is defined in greater detail below.

DEFINITIONS

For purposes of this invention, a fatty acyl isethionate "product" comprises (in addition to other components) both pure fatty acyl isethionates surfactant as well as free fatty acid and/or fatty acid salt.

Fatty Acyl Isethionate Surfactant Product

Compositions of the invention comprise 15 to 50% by wt. fatty acyl isethionate surfactant product with more than 10 wt %, preferably more than 15 wt % of free fatty acid/fatty soap in the surfactant product.

Fatty acyl isethionate surfactant are typically prepared by the reaction of an isethionates salt such as alkali metal isethionates and an aliphatic fatty acid having 8 to 20 carbon atoms and Iodine Value (measuring degree of unsaturation) of less than 20 g, for example:

where $R^1$ is an aliphatic hydrocarbon radical containing 2 to 4 carbons;

M is alkali metal cation or metal ion (e.g., sodium, magnesium, potassium, lithium), ammonium or substituted ammonium cation or other counterion; and R is an aliphatic hydrocarbon radical having 7 to 24, preferably 8 to 22 carbons.

Figure 3:
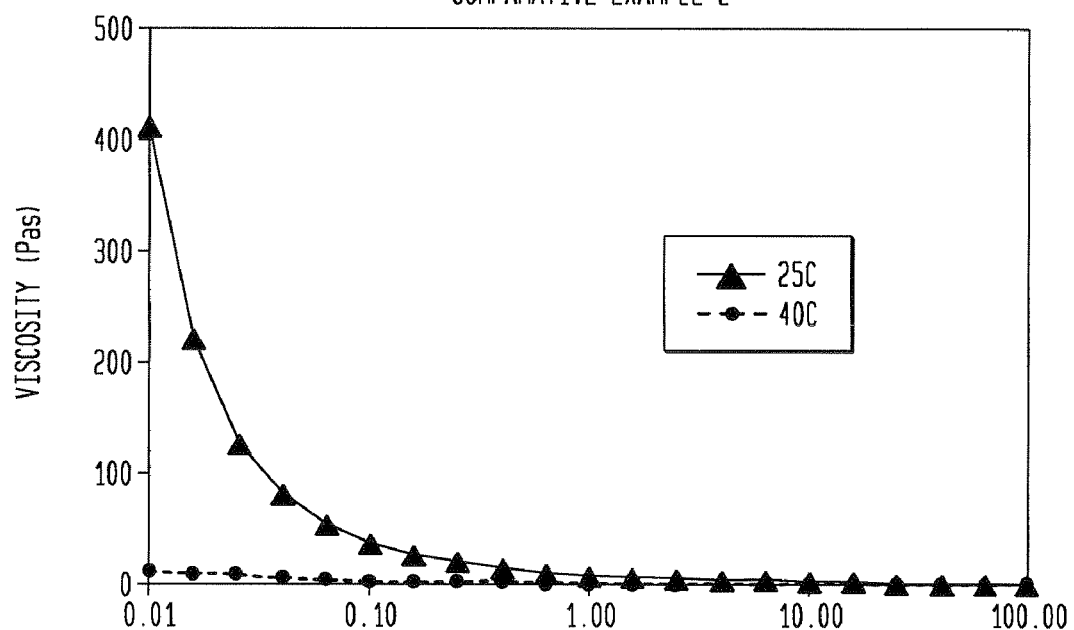
FIG. 3 is temperature effect on the viscosity profile of liquid composition containing mixture fatty acyl isethionate surfactant product and cocoamidopropylbetaine and sodium lauryl ethoxylated sulfate cosurfactants without the specific surfactant crystal modifiers forming stabilizing system of this invention which is the comparative example 4A of Table 2. The figure shows this sample had a viscosity very sensitive to the storage temperature. At 25° C. it had lotion-like texture; however, at 40° C., it became water-thin liquid. The viscosity ratio of 40° C. to 25° C. is 0.021 and the sample showed phase separation at 45° C. storage condition.
Figure 4:
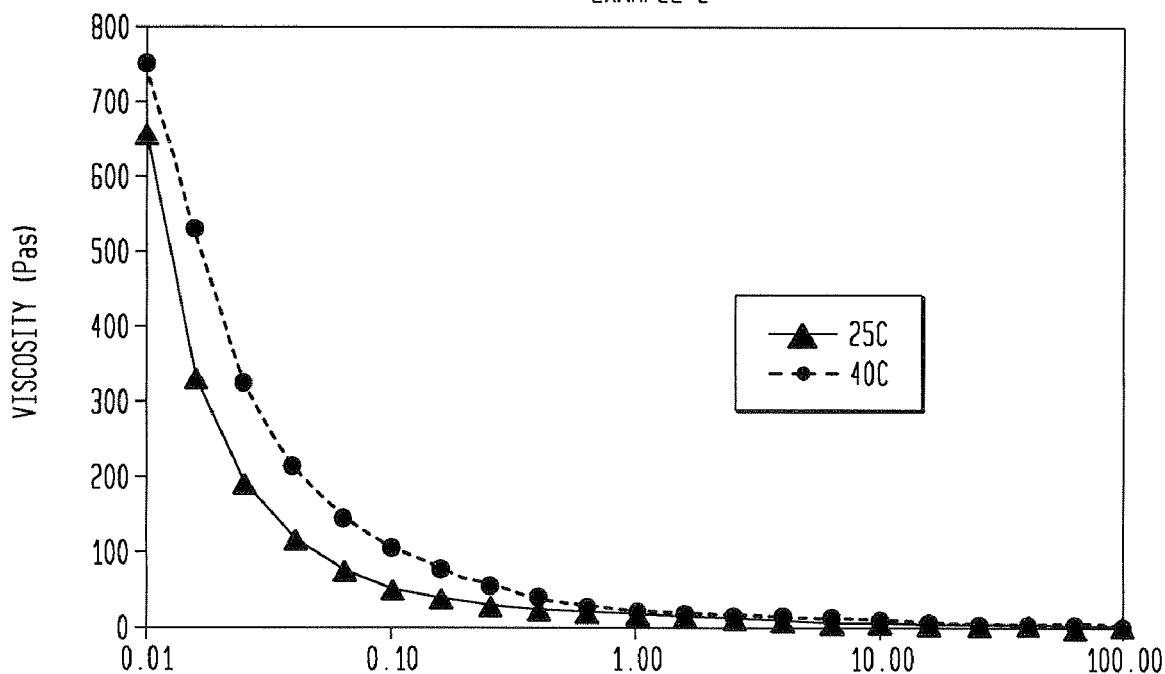
FIG. 4 is a viscosity profile of liquid composition which is the liquid composition shown in FIG. 3 containing the surfactant crystal modifiers of this invention, i.e. combination of cocomonoethanolamide and hydrocarbon oil (Example 4 of Table 1). At 25° C., the sample also had lotion-like texture and, at 40° C., it maintained its viscosity and was stable at 45° C. for over 4 weeks.
Figure 5A:
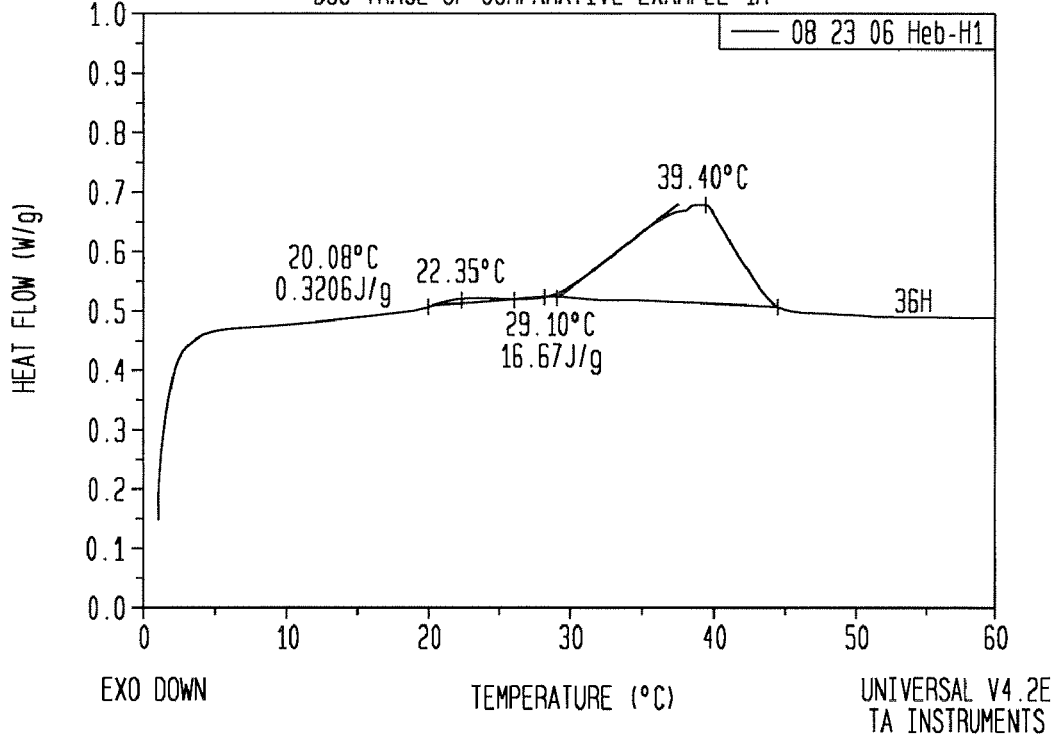
FIGS. 5A and 5B are DSC trace of Comparative Example 1A and Example 1 of this invention. These two DSC traces show that both samples contain fatty acyl isethionate/fatty acid surfactant crystals with dissolution temperature in the range of 30 to 50° C. When the stabilizing system of the invention is used, the liquid maintains high viscosity at elevated temperature upon dissolution of the surfactant crystals. It is believed that the specific combination defining the surfactant elevated temperature stability system changes the packing of the surfactant mixture of the liquid composition of this invention upon the dissolution of insoluble fatty acyl isethionate/fatty acid crystals at a temperature above its dissolution temperature to form viscous surfactant liquid crystal instead of low viscosity surfactant micelles such that the liquid maintains a high viscosity and maintains its physical stability.

Depending on the processing conditions used, the resulting fatty acyl isethionate product can be a mixture of 45 to 95% by weight of fatty acyl isethionates and 50 to about 0 wt %, typically 40 to 5 wt % of free fatty acids, in addition to isethionates salts which are present typically at less than 5 wt. %, and traces (less than 2 wt. %) of other impurities. Generally a mixture of aliphatic fatty acids is used for the preparation of commercial fatty acyl isethionates surfactants; and the resulting fatty acyl isethionate surfactants (e.g., resulting from reaction of alkali metal isethionate and aliphatic fatty acid) have at least 20 wt % (on basis of fatty acyl isethionates reaction product) of fatty acyl group with 14 or more carbon atoms and at least 16 wt. % of fatty acids with 14 or greater carbon atoms. They form insoluble surfactant crystals in water at ambient temperatures. These fatty acyl isethionate/fatty acid crystals have a dissolution temperature between 30° and 45° C. as shown in FIG. 5A by measuring the crystal transition temperature of an aqueous solution containing only fatty acyl isethionate surfactant product in the liquid with a pH in the range of 6.0 to 7.5 (comparative example 1A of Table 2) using differential scanning calorimetry (DSC)

method described below. Due to the presence of these fatty acyl isethionate/fatty acid crystals, liquids containing these commercial fatty acid isethionate products as the primary surfactant (60% or greater of surfactant system) in the liquid composition have very high viscosity at or below room temperature. At or above 40° C., however, the liquid turns into water thin liquid due to the dissolution of these surfactant crystals as shown in both FIG. 1 and FIG. 3. This causes product inconsistency and storage instability at elevated temperatures (40° C. or above).

A key aspect of the present invention is that the extreme inconsistency of the fatty acyl isethionate product-containing liquid cleanser and its instability at elevated storage temperatures (40° C. or above) due to the dissolution of insoluble fatty isethionate/fatty acid crystals can be resolved using a specific combination of surfactant crystal modifier system (i.e., the elevated temperature storage stabilization system of the invention) such that the resulting liquid composition can maintain its consistency and its stability by forming viscous surfactant liquid crystals at elevated storage temperatures (40° C. or above).

Particularly preferred fatty acyl isethionate products with 10 wt. % or more fatty acid/fatty soap which may now be consistently used include DEFI (Direct Esterification of Fatty Isethionate) flakes and synthetic detergent noodles produced from DEFI for personal cleanser application. DEFI flakes typically contain about 65 to 80 wt % of sodium fatty acyl isethionate and 15 to 30 wt % free fatty acids. More than 65 wt % of fatty acyl group of the resulting fatty acyl isethionates have 12 to 18 carbon atoms. Dove® cleansing bar noodles are mixtures of DEFI flakes described above and long chain (mainly C16 and C18) fatty acids and fatty soaps which contain about 40 to 60 wt % of fatty acyl isethionates and 30 to 40 wt % of fatty acids and fatty soaps. Examples of other commercial fatty acyl isethionate products that may be used in the invention are Hostapon® surfactants from Clariant such as Hostapon® SCI65C; Jordapon® CI65; and sodium cocoyl isethionate from Yongan Daily Chemical Co. such as YA-SCI-75® or YA-SCI-65®.

As indicated, these fatty acyl isethionate surfactant products have not typically been used in preparation of personal liquid compositions, particularly compositions where fatty acyl isethionate product comprises 60% or greater of surfactant system, because they readily form solid crystals (when used alone and/or with co-surfactant) and consequently make it very difficult to form stable liquids with consistent viscosity at both ambient and elevated temperatures.

The amount of fatty acyl isethionate surfactant product used in the liquid cleanser compositions of the present invention can be in the range of 15% up to 50 wt %, preferably 15% to 45 wt % of the liquid composition. The preferred level depends on the total amount of fatty acyl isethionate surfactants product and other synthetic co-surfactants in the liquid cleanser of the present invention. The amount used should also comprise 60 to 100 wt % of the total amount of the surfactant system, i.e., the combined fatty acyl isethionate surfactant product and the synthetic co-surfactants described below.

Synthetic Co-Surfactants

A second component of the subject invention are surfactants selected from the groups consisting of anionic surfactants, nonionic surfactants, zwitterionic surfactants, amphoteric surfactants as described below. Such synthetic co-surfactants are believed to partially solubilize fatty acyl isethionate surfactant crystal described above. The amount of synthetic co-surfactant used in the present invention can be in the range of 0 to 15 wt % depending on the level of pure fatty acyl isethionate surfactant in the liquid composition. The amount of co-surfactant in the liquid composition should also be 0 to 40 wt % preferably 0 to 30 wt % of total weight of pure fatty acyl isethionates product and synthetic co-surfactants of the liquid cleanser composition combined.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than at least 0.5, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, alkyl and acyl glycinates, alkyl sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, and branched acyl isethionates.

The anionic may also be fatty acyl isethionate surfactant product with fatty acid level less than 10 wt % such as Jordapon CI, which is Na cocoyl isethionate with less than 8 wt % of fatty acid.

Another class of anionics are carboxylates such as follows:

$$R-(CH_2CH_2O)_nCO_2M$$

wherein R is $C_8$ to $C_{20}$ alkyl; n is 1 to 20; and M is as defined above.

Another carboxylate which can be used is amido alkyl polypeptide carboxylates such as, for example, Monteine LCQ® by Seppic.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

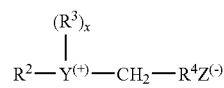

$$R^2-Y^{(+)}\underset{\underset{(R^3)_x}{|}}{-}CH_2-R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

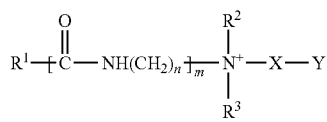

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Amphoacetates and diamphoacetates are also intended to be covered in possible zwitterionic and/or amphoteric compounds which may be used.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

Elevated Temperature Storage Stability System

Figure 5B:
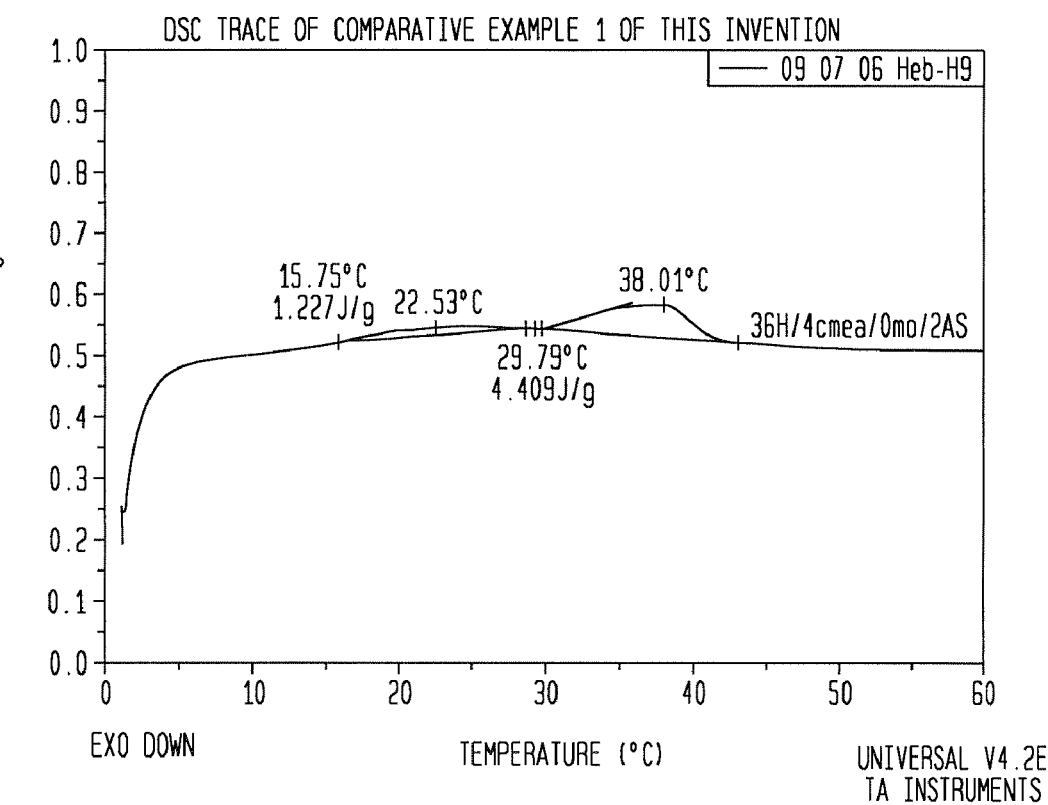

Another essential ingredients of the present invention is the surfactant crystal modifier system (i.e., elevated temperature storage stabilizing system) which system comprises the combination of alkanolamides and/or alkylamineoxides with a component selected from the group consisting of hydrocarbon oils, ammonium salts, organic amines, linear C8 to C13 fatty acid/fatty alcohols, branch chain fatty acids and mixtures thereof. It was found that this specific combination defining the surfactant "elevated temperature storage stability system" increases the viscosity of the liquid composition at or above 40° C. such that the viscosity of the liquid composition remains viscous enough to maintain its physical stability when stored at or above 40° C. (compare FIG. 1 to 2 and FIG. 3 to 4). It is believed that the specific combination defining the surfactant elevated temperature stability system changes the packing of the surfactant mixture of the liquid composition of this invention upon the dissolution of insoluble fatty acyl isethionate/fatty acid crystals at a temperature above its dissolution temperature to form viscous surfactant liquid crystal instead of low viscosity surfactant micelles such that the liquid maintains a high viscosity and maintains its physical stability. Presence of insoluble fatty acyl isethionate crystals in the liquid composition of this invention can be confirmed either using a cross-polarized light optical microscope or by the DSC trace of the sample. The DSC trace of the sample measured using the method described below should have crystal thermal transition at a temperature between 30 to 50 C as shown in FIG. 5B.

Examples of alkanolamides and alkylamineoxides which may be used include but are not limited to mono- and di-ethanolamides, N-methyl monoethanolamide, isopropanolamides of fatty acids having about 10 to 20 carbon atoms, and PPG-hydroxyethyl cocamides; and alkylamineoxide with carbon chain length in the range of 10 to 20. Specific examples of suitable compounds include cocomonoethanolamide, cocodiethanolamide, lauryl mono/or di ethanol amide, coco mono/or di isopropanolamide, lauryl mono/or di ethanolamide, myristyl mono/or di ethanolamide, cocoyl N-methyl mono ethenolamide, cocoylamineoxide, laurylamineoxide, myristylamineoxide, and polypropylene glycol-2-hydroxyethyl cocoamide. Particularly useful ingredients for this invention are cocomono or diethanol amide, lauryl mono/or di ethanol amide, lauryl amine oxide and coco amine oxide.

Hydrocarbon oils that are useful as the second component of the stabilizing system of this invention should have a molecular weight less than 600, preferably less than 400 g per mole. Examples are hydrocarbon oils of 9 to 30 hydrocarbons, preferably 10 to 24 linear hydrocarbon oil. It can be pure hydrocarbon oils such as hexadecane or dodecane, or low molecular weight mineral oil such as 40 oil or Klearol® white mineral oil from Sonneborn.

Ammonium salts or organic amines which may be used include but are not limit to ammonium sulfate, ammonium chloride, ammonium phosphate, tri-ethanol amine, mono- or di-ethanol amine.

Fatty acids or fatty alcohols that may be used as crystal modifiers are linear fatty acid or fatty alcohol with 8 to 13 carbons such as lauric acid, capric acid, lauric alcohol, or branched fatty acids of C12 to C20 hydrocarbons such as oleic acid and isostearic acid. Due to its negative effect on the lather of liquid cleansers, the total amount of fatty alcohols and branched fatty acids in the liquid composition of this invention is no more than 2 wt %, preferably less no more than 1 wt %.

The total amount of combined stabilizing system components in the present invention can be 1.0 to 16 wt % of the liquid composition, in which at least 0.1, preferably 0.3 wt. % of the system comprises alkanoamide or alkylamineoxides, depending on total amount of fatty acyl isethionates and synthetic co-surfactants in the liquid composition. Specifically the total amount of elevated temperature storage stability system should be at least 5 wt %, preferably at least 10 wt % of the total pure fatty acyl isethionates and synthetic co-surfactants in the liquid composition of this invention. Thus, for example, if liquid comprises 15% by wt. pure fatty acyl isethionate and 5% by wt. synthetic, there should be at least 1% by wt. stabilizing system.

Both the level and the composition of the elevated temperature storage stability system required in the liquid composition of this invention can be determined by measuring the viscosity of the liquid cleanser composition of this invention containing various amount of the surfactant elevated temperature storage stability system components using the viscosity method described below at both 25° C. and 40° C. The viscosity at 0.01 s$^{-1}$ should be at least 250 Pas, preferably 350 Pas at 25° C.; and the ratio of the viscosity at 40° C. to the viscosity at 25° C. at 0.01 s$^{-1}$ should be at least 0.1, preferably 0.2, most preferably 0.4. The higher the ratio, the better the stability at elevated temperature. Other than the viscosity criteria described above, the liquid composition containing the desired combination of the liquid crystal modifiers should be stable at 45° C. for over 2 weeks.

Water Soluble/Dispersible Polymers

Water soluble/dispersible polymers are an optional ingredient that is preferred to be included in the liquid composition of the invention. The water soluble/or dispersible polymer can be cationic, anionic, amphoteric or nonionic polymer with molecular weight higher than 100,000 Dalton. These polymers are known to enhance in-use and after-use skin sensory feels, to enhance lather creaminess and lather stability, and to increase the viscosity of liquid cleanser compositions.

Examples of water soluble/or dispersable polymers useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum arabic, gum acacia, gum agar, xanthan gum and mixtures thereof; modified and nonmodified starch granules with gelatinization temperature between 30 to 85° C. and pregelatinized cold water soluble starch; polyacrylate; Carbopols; alkaline soluble emulsion polymer such as Aculyn 28, Aculyn 22 or Carbopol Aqua SF1; cationic polymer such as modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series by Henkel, Inc.; Quadrosoft Um-200; and Polyquaternium-24.

Gel forming polymers such as modified or nonmodified starch granules, xanthan gum, Carbopol, alkaline-soluble emulsion polymers and cationic guar gum such as Jaguar C13S, and cationic modified cellulose such as UCARE Polymer JR 30 or JR 40 are particularly preferred for this invention.

Water Soluble Skin Benefit Agents

Water-soluble skin benefit agents another optional ingredient that is preferred to be included in the liquid compositions of the invention, A variety of water-soluble skin benefit agents can be used and the level can be from 0 to 40 weight %, preferably 1 to 30%. The materials include, but are not limited to, polyhydroxy alcohols such as glycerol, propylene glycol, sorbitol, pantenol and sugar; urea, alpha-hydroxy acid and its salt such as glycolic or lactic acid; and low molecular weight polyethylene glycols with molecular weight less than 20,000. Preferred water soluble skin benefit agents for use in the liquid composition are glycerol, sorbitol and propylene glycol.

The liquid cleansing composition of the invention also may comprise 0 to 40% by wt. benefit agent.

One class of ingredients are nutrients used to moisturize and strengthen, for example, the skin. These include:
a) vitamins such as vitamin A and E, and vitamin alkyl esters such as vitamin C alkyl esters;
b) lipids such as cholesterol, cholesterol esters, lanolin, creaminess, sucrose esters, and pseudo-ceramides;
c) liposome forming materials such as phospholipids, and suitable amphophilic molecules having two long hydrocarbon chains;
d) essential fatty acids, poly unsaturated fatty acids, and sources of these materials;
e) triglycerides of unsaturated fatty acids such as sunflower oil, primrose oil avocado oil, almond oil;
f) vegetable butters formed from mixtures of saturated and unsaturated fatty acids such as Shea butter;
g) minerals such as sources of zinc, magnesium, and iron;

A second type of skin benefit agent is a skin conditioner used to provide a moisturized feel to the skin. Suitable skin conditioners include:
a) silicone oils, gums and modifications thereof such as linear and cyclic polydimethylsiloxanes, amino, alkyl, and alkyl aryl silicone oils;
b) hydrocarbons such as liquid paraffins, petrolatum, Vaseline, microcrystalline wax, ceresin, squalene, pristan, paraffin wax and mineral oil;
c) conditioning proteins such as milk proteins, silk proteins and glutens;
d) cationic polymers as conditioners which may be used include Quatrisoft LM-200 Polyquaternium-24, Merquat Plus 3330-Polyquaternium 30; and Jaguar® type conditioners;
e) humectants such as glycerol, sorbitol, and urea;
f) emollients such as esters of long chain fatty acids, such as isopropyl palmitate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:

a) antimicrobials such as 2-hydrozy-4,2',4'-trichlorodiphenylether (DP300) 2,6-dimethyl-4-hydroxychlorobenzene (PCMX),3,4,4'-trichlorocarbanilide (TCC), 3-trifluoromethyl-4,4'-dichlorocarbanilide (TFC), benzoyl peroxide, zinc salts, tea tree oil, b) anti-acne agents such as salicylic acid, lactic acid, glycolic acid, and citric acid, and benzoyl peroxide (also an antimicrobial agent), c) oil control agents including sebum suppressants, modifiers such as silica, titanium dioxide, oil absorbers, such as micro sponges, d) astringents including tannins, zinc and aluminum salts, plant extracts such as from green tea and Witch-hazel (Hammailes), e) scrub and exfoliating particles, such as polyethylene spheres, agglomerated silica, sugar, ground pits, seeds, and husks such as from walnuts, peach, avocado, and oats, salts, f) cooling agents such as methanol and its various derivatives and lower alcohols, g) fruit and herbal extracts, h) skin calming agents such as aloe vera, i) essential oils such as mentah, jasmine, camphor, white cedar, bitter orange peel, rye, turpentine, cinnamon, bergamot, citrus unshiu, calamus, pine, lavender, bay, clove, hiba, eucalyptus, lemon, starflower, thyme, peppermint, rose, sage, menthol, cineole, sugenol, citral, citronelle, borneol, linalool, geranoil, evening primrose, camphor, tymol, spirantol, penene, limonene and terpenoid oils.

Other benefit agents that can be employed include antiaging compounds, sunscreens, and in lightening agents.

When the benefit agent is oil, especially low viscosity oil, it may be advantageous to pre-thicken it to enhance its delivery. In such cases, hydrophobic polymers of the type describe in U.S. Pat. No. 5,817,609 to He et al. may be employed, which is incorporated by reference into the subject application.

The final liquid cleanser composition of the present invention should have a viscosity more than 250, preferably greater than 350 Pas measured at 0.01 rps determined by a Rheometric Scientific SR5 Rheolmeter at 25° C., preferably at 10° C., 25° C. and 40° C., following the methodology for viscosity determination described below; and pH between 4.0 to 8.0, preferably 5.0 to 7.5. At ambient temperature, the composition contains surfactant crystals with dissolution temperature between 30° C. to 50° C. The compositions should also be physically phase stable at room temperature and 45° C. for at least two 2 weeks.

Other Optional Components

In addition, the compositions of the invention may include 0 to 10% by wt. optional ingredients as follows:

Perfumes; sequestering agents, such as tetra sodium ethylenediaminetetraacetate (EDTA), EHDP or mixtures in an amount of 0.01 to 1%, preferably 0.01 to 0.05%; and coloring agents, opacifiers and pearlizers such as zinc striate, magnesium stearate, TiO$_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenyl ether (DP300); preservatives such as dimethyloldimethylhydantoin (Glydant XL 1000), parabens, sorbic acid etc.

Antioxidants such as, for example, butylated hydroxytoluene (BHT) may be used advantageously in amounts of about 0.01% or higher if appropriate.

Polyethylene glycols as conditioners which may be used include:

| | | |
|---|---|---|
| Polyox | WSR-25 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

EXAMPLES & PROTOCOL

Methodology of Differential Scanning Calorimetry (DSC)

Samples were weighed into an aluminum pan, hermetically sealed, and loaded into a 2920 MDSC machine from TA Instruments at 25° C. The sample was equilibrated to a temperature of 2° C., Iso-Track for 2 minutes followed by heating at 5° C./min to 60° C.

Methodology for Viscosity Measurement

Viscosity was measured using either SR-5 Rheometer from Rheometric Scientific or AR-G2 Rheolometer from TA Instruments. Procedures and set up for each rheometer to measure the cleanser's viscosity are described below:

Instrument: SR-5 from Rheometric Scientific

Geometry: Cone and Plate

Diameter: 25 mm

Cone Angle: 5.69°

GAP: 0.056 mm

Experimental Conditions:

Test type: Steady Rate Sweet

Shear Rate Ramp: from 0.01 to 100 (log mode, 5 points per decade)

Measurement Time: 20 seconds

Temperature: Various (10° C./25° C./40° C.)

Procedure:

About 0.5 g of sample was poured on to the plate. Cone was lowered to the gap of 0.1 mm and excess of sample was removed using plastic spatula. Gap was reduced to 0.056 mm and test was started. Shear rate vs. viscosity were plotted.

Alternative Instrument: AR-G2 from TA Instruments

Geometry: Cone and Plate

Diameter: 40 mm

Cone Angle: 2°

GAP: 0.061 mm

Experimental Conditions:

Test Type: Steady Rate Sweep

Shear Rate Ramp: from 0.01 to 100 (log mode, 5 points per decade)

Measurement Time: 40 seconds

Temperature: Various (10° C./25° C./40° C.)

Procedure:

About 0.5 g of sample was poured on to the plate. Cone was lowered to the gap of 0.1 mm and excess of sample was removed using plastic spatula. Gap was reduced to 0.061 mm and test was started. Shear rate vs. viscosity were plotted.

Examples of compositions of the invention are set forth below:

TABLE 1

Examples 1 to 9 of this invention

| | Example # | | | | | | | | |
|---|---|---|---|---|---|---|---|---|---|
| | 1 | 2 | 3 | 4 | 5 | 6 | 7 | 8 | 9 |
| Dove ® bar noodle* | 36 | 36 | 36 | 30 | 30 | 20 | — | — | — |
| DEFI | — | — | — | — | — | — | 30 | 26 | 26 |
| Na Cocoyl isethinate (Jordapon Cl ex. ICI) | — | — | — | — | — | 1 | — | — | — |
| Cocoamido propyl betaine | — | — | — | 1 | — | 3.5 | 0 | 0 | 2 |
| Na lauryl 1EO sulfate | — | — | — | 2 | — | 6.5 | 0 | 2 | 0 |
| Cocomonoethanol amide | 4 | 4 | 2 | 4 | 2 | 2.5 | 5 | 5 | 5 |
| Lauric acid | — | — | — | — | — | 1 | 2 | 2 | 2 |
| Lauryl aminoxide | — | — | — | — | 2 | — | — | — | — |
| Mineral oil (40 oil ex. Sonneborn) | 0 | 2 | 1 | 2 | 2 | 1 | 2 | 2 | 2 |
| $(NH_4)_2SO_4$ | 2 | 0 | 0 | 0 | 0 | 2 | 2 | 2 | 2 |
| Jaguar C13S (ex. Rhodia) | — | — | — | — | — | 0.1 | — | — | — |
| EDTA | 0.05 | 0.05 | 0.05 | 0.05 | 0.05 | 0.05 | 0.05 | 0.05 | 0.05 |
| Glydant | 0.2 | 0.2 | 0.2 | 0.2 | 0.2 | 0.1 | 0.2 | 0.2 | 0.2 |
| Perfume | 0.8 | 0.8 | 0.8 | 0.8 | 0.8 | 1.2 | 0.8 | 0.8 | 0.8 |
| % fatty acyl isethionate product** | 100% | 100% | 100% | 90.9% | 100% | 64.5% | 100% | 92.8% | 92.8% |
| 25° C. viscosity Pas at 0.01 rps | 793 | 416 | 1367 | 655 | 950 | 1477 | 1263 | 416 | 1895 |
| 40° C./25° C. viscosity ratio | 1.61 | 0.70 | 0.223 | 1.14 | 0.45 | 1.23 | 1.65 | 10.2 | 1.74 |

*Dove ® bar, as unfragranced noodles
**wt % of fatty acyl isethionate product of total fatty acyl isethionate product and synthetic surfactant in the liquid composition All examples in Table 1 were prepared by mixing all the ingredients except perfume, glydant plus, EDTA and ammonium sulfate (if used) at 70 to 75° C. for 20 to 30 minutes until all the solid ingredients such as Dove® noodle, DEFI flake, and cocomonoethanolamide (CMEA) dissolved to form an uniform mixture. Perfume, glydant plus (a hydantoin preservative) and ammonium sulfate were added after the liquid was cooled below 40° C. The pH of these liquids was adjusted to 6.0 to 7.0 using either 30% citric acid or 25% NaOH solution. Both DEFI and Dove® are fatty acyl isethionate products manufactured by Unilever. DEFI has 68-72 wt % of C8 to C18 fatty acyl isethionates and 18-22 wt % free fatty acids of 8 to 18 carbons. Dove® is prepared by mixing 68-72 wt % of DEFI with 18-25 wt % of long chain (C16 to C18) fatty acid and fatty soap. Dove® contains about 48 to 52 wt % of fatty acyl isethionate surfactant and 32 to 36 wt % of fatty acid/fatty soap.

Samples were stored at room temperature and 45° C. for over 4 weeks. At 25° C., all the samples as shown in Table 1 have a viscosity more than 400 Pas at 0.01 s$^{-1}$ and a viscosity ratio of 40° C. to 25° C. measured at 0.01 s$^{-1}$ higher than 0.2. They were stable at both 25 and 45° C. after storage for over 4 weeks, without visible physical separation. These examples indicate that this invention are sufficiently robust to stabilize fatty acyl isethionate surfactant products containing high level of fatty acid/fatty soap (i.e., when used with surfactant crystal modifiers, compositions are consistently stable at both high and low temperature for at least 4 weeks regardless of fatty acid content and/or chain length of fatty acyl group).

Comparative examples with compositions similar to Examples 1, 2, 4, 6 and 7 as shown in Table 2, without the surfactant crystal modifier system of this invention, i.e. combination of CMEA with hydrocarbon oil, ammonium ion and/or lauric acid were prepared for comparison. All the comparative examples were prepared the same way described above. None of these samples were stable at 45° C. for over 2 weeks and showed phase separation in less than 2 weeks due to the lack of one of the required ingredients required to stabilize the liquid composition. Specifically, Comparative Example 1A had none of the elevated temperature storage stability system of this invention; Comparative Examples 2B, 4A, 6A and 7A had no CMEA; and Comparative Examples 1B, 2A and 4B contained only CMEA without other required ingredients of this invention. All the comparative examples had non-consistent viscosity at elevated and ambient temperature. They all had a viscosity ratio at 25° C. to 40° C. less than 0.20 except Comparative Examples 6A and 7A. The viscosity of Comparative examples 6A and 7A at 25° C. is less than 350 Pas, the preferred minimum liquid viscosity of this invention.

TABLE 2

Comparative examples

| | Comparative example# | | | | | | | | |
|---|---|---|---|---|---|---|---|---|---|
| | 1A | 1B | 1C | 3A | 4A | 4B | 6A | 7A | 10A |
| Dove bar noodle* | 36 | 36 | 36 | 36 | 30 | 30 | 20 | — | 30 |
| DEFI | — | — | — | — | — | — | — | 30 | — |
| Jordopon Cl | — | — | — | — | — | — | 1 | — | — |
| CAP betaine | — | — | — | — | 1 | 1 | 3.5 | — | — |
| NaLE1S | — | — | — | — | 2 | 2 | 6.5 | — | — |
| Na lauryl sulfosuccinate | — | — | — | — | — | — | — | — | 8 |
| CMEA | — | 4 | — | 2 | — | 4 | — | — | 2 |
| Mineral oil 40 | — | — | 2 | — | — | — | — | 2 | 0.5 |
| NH4SO4 | — | — | 2 | — | — | — | — | 2 | 2 |
| Jaguar C13S | — | — | — | — | — | — | 0.1 | — | 0.1 |
| EDTA | 0.05 | 0.05 | 0.05 | 0.05 | 0.05 | 0.05 | 0.05 | 0.05 | 0.05 |
| Glydant | 0.2 | 0.2 | 0.2 | 0.2 | 0.2 | 0.2 | 0.1 | 0.2 | 0.2 |
| Perfume | 0.8 | 0.8 | 0.8 | 0.8 | 0.8 | 0.8 | 1.2 | 0.8 | 0.3 |
| % fatty acyl isethionate product** | 100% | 100% | 100% | 100% | 90.9% | 90.9% | 64.5% | 100% | 79% |
| 25° C. viscosity Pas at 0.01 rps | 875 | 1552 | 888 | 1170 | 412 | 715 | 306 | 46 | 458 |
| 40° C./25° C. viscosity ratio | 0.023 | 0.215 | 0.033 | 0.077 | 0.021 | 0.08 | 0.25 | 0.913 | 0.03 |

*Dove ® bar, as unfragranced noodles
**wt % of fatty acyl isethionate product of total fatty acyl isethionate product and synthetic surfactant in the liquid composition Examples 10 to 16 with compositions given in Table 3 were prepared using the same method described above. Mixture of Dove® bar noodle with various synthetic surfactants were prepared using the viscosity modifier system of this invention. All the examples in Table 3 are stable at both 25 and 40° C. for over 4 weeks without any visible phase separation.

It should be noted in general that the level of alkanoamide such as CMEA, or of hydrocarbon oils, to form the stable liquid composition of this invention also depends on the combination of fatty acyl isethionate and synthetic co-surfactant. This is exemplified in Examples 10 and 11 of Table 3 and Comparative example 10A of Table 2 using the same crystal modifier system (stabilizing system), i.e., 2% CMEA, 0.5% M40 mineral oil and 2% ammonium sulfate but different synthetic cosurfactant. Combination of Dove® bar noodle with either Na cocoyl isethinate (Example 10) or K cocoyl glycinate is stable, but not with Na lauryl sulfosuccinate (Comparative Example 10 A).

TABLE 3

Examples 10 to 16 of this invention

| | Example # | | | | | | |
|---|---|---|---|---|---|---|---|
| | 10 | 11 | 12 | 13 | 14 | 15 | 16 |
| Dove ® bar noodle* | 30 | 30 | 30 | 30 | 20 | 20.9 | 17.4 |
| Na Cocoyl isethinate (Jordapon Cl ex. ICI) | 8 | — | 4 | 4 | — | — | 0.87 |
| Cocoamido propyl betaine | — | — | — | — | 3.5 | — | 3.0 |
| Na lauryl 1EO sulfate | — | — | — | — | 7.5 | 8.7 | 5.7 |
| Potassium cocoyl glycinate | — | 8 | 4 | — | — | — | — |
| Na cocoglycinate | — | — | — | 4 | — | — | — |
| Lauric acid | 1 | 1 | 1 | 1 | 1.0 | 0.87 | 0.87 |
| Isostearic acid | — | — | — | — | 1 | — | — |
| CMEA | 2 | 2 | 2 | 2 | 0.92 | 1.74 | 2.2 |
| Mineral oil 40 | 0.5 | 0.5 | 0.5 | 0.5 | — | — | — |
| Ammonium sulfate | 2 | 2 | 2 | 2 | 1 | 2 | 2 |
| Jaguar C13S | 0.1 | 0.1 | 0.1 | 0.1 | 0.1 | 0.09 | 0.09 |
| Petrolatum | — | — | — | — | — | 1 | 1.7 |
| Soybean oil | — | — | — | — | — | 3 | 10.4 |
| Glycerin | — | — | — | — | — | 2 | 2.6 |
| EDTA | 0.05 | 0.05 | 0.05 | 0.05 | 0.05 | 0.05 | 0.05 |
| Glydant | 0.2 | 0.2 | 0.2 | 0.2 | 0.2 | 0.2 | 0.2 |
| Perfume | 0.3 | 0.3 | 0.3 | 0.3 | 1.2 | 1.2 | 1.2 |
| % fatty acyl isethionate product** | 79% | 79% | 79% | 79% | 64.5% | 70.6% | 64.5% |
| 25° C. viscosity Pas at 0.01 rps | 4282 | 447 | 1937 | 1983 | 1675 | 1805 | 1770 |
| 40° C./25° C. viscosity ratio | 0.52 | 4.83 | 0.76 | 0.46 | 0.54 | 1.40 | 1.49 |

*Dove ® bar, as unfragranced noodles
**wt % of fatty acyl isethionate product of total fatty acyl isethionate product and synthetic surfactant in the liquid composition

The invention claimed is:

1. A personal liquid cleanser composition comprising:
   (a) 15 to 50 wt % of fatty acyl isethionate surfactant product containing 10 to 50 wt % fatty acids and/or fatty soaps and 35 to 85 wt % fatty acyl isethionate in the said product, said product comprising at least 60% of total surfactant product of item a and co-surfactants of item b in the liquid composition;
   (b) 0 to 15 wt % of a co-surfactant selected from the group consisting of anionic (excluding fatty acyl isethionate of (a)), amphoteric and nonionic surfactants and mixture thereof wherein the amount of said cosurfactant is 0 to 40 wt % of total amount of fatty acyl isethionate surfactant product of item a and cosurfactant of item b;
   (c) 1% to 16% by wt. of an elevated temperature stabilizing system comprising:
      (i) 0.1 to 8 wt % of a compound selected from the group consisting of mono- and di-ethanolamides, N-methyl-monoethanolamide, isopropanolamides of fatty acids having about 10 to 20 carbon atoms, and PPG-hydroxyethyl cocamides wherein the amount of said alkanolamide is;
      (ii) 0.3 to 8 wt % of a compound selected from the group consisting of C9 to C30 aliphatic hydrocarbon oils, ammonium salt, organic amine, linear C8 to C13 fatty acid/fatty alcohol, branched fatty acid and mixtures thereof, wherein the total amount of fatty alcohols and branched fatty acids is no more than 2 wt % in the liquid composition;
   wherein the ratio of fatty acyl isethionate surfactant product of item a to cosurfactant of item b is in the range of 10/0 to 6/4; the viscosity of the said liquid cleanser composition at $0.01\ s^{-1}$ is at least 350 Pas; and the ratio of the viscosity at 40° C. to the viscosity at 25° C., when measured at $0.01\ s^{-1}$, is at least 0.2, wherein said composition is stable (i.e., (is physically stable and will not partition as can be visually observed) at 45° C. for at least 2 weeks; and
   wherein at ambient temperature, said composition contains surfactant crystals with dissolution temperature between 30° C. to 50° C.; wherein said composition, in the absence of the elevated temperature stabilization system (d), either has ratio of viscosity at 40° C. to viscosity at 25° C. less than 0.2 or has a viscosity at 25° C. less than 350 Pas when measured at $0.01\ s^{-1}$ and shows phase separation at 45° C. in less than two weeks.

2. A composition according to claim 1, wherein a fatty acyl isethionate product used in a process for making said composition comprises mixtures of 45-85% fatty acyl isethionate and 15 to 40% free fatty acids.

3. A composition according to claim 1, wherein total amount of items (c)(i) and (c)(ii) is $\geqq 10$ wt % of total amount of pure fatty acyl isethionate surfactant and synthetic co-surfactants of item a and b of claim 1.

4. A composition according to claim 1, wherein total amount of items (c)(i) and (c)(ii) is $\geqq 15$ wt % of total amount of pure fatty acyl isethionate surfactant and synthetic co-surfactants of item a and b of claim 1.

5. A composition according to claim 1, additionally comprising 1 to 20% emollient.

6. A composition according to claim 1, wherein the aliphatic hydrocarbon oil is linear hydrocarbon having $C_9$ to $C_{20}$ chain length.

7. A composition according to claim 1, wherein water-soluble and/or dispersible polymer is a polymer selected from the group consisting of starch granule xanthan gum, Carbopol, cross-linked soluble emulsion polymers, cationic guars and mixtures thereof.

* * * * *